United States Patent [19]

Doumaux, Jr. et al.

[11] 4,353,843

[45] Oct. 12, 1982

[54] PREPARATION OF NITRITE ESTERS

[75] Inventors: Arthur R. Doumaux, Jr., Charleston; James M. Downey, St. Albans; Joseph P. Henry, South Charleston; John M. Hurt, St. Albans, all of W. Va.

[73] Assignee: Union Carbide Corporation, Danbury, Conn.

[21] Appl. No.: 239,761

[22] Filed: Mar. 12, 1981

Related U.S. Application Data

[63] Continuation-in-part of Ser. No. 227,798, Jan. 23, 1981, abandoned.

[51] Int. Cl.³ .............................................. C07C 77/00
[52] U.S. Cl. .................................................. 260/466
[58] Field of Search ............... 260/466, 467; 568/947, 568/948

[56] References Cited

U.S. PATENT DOCUMENTS

| | | | |
|---|---|---|---|
| 2,166,698 | 7/1939 | Allen | 260/466 |
| 2,739,166 | 3/1956 | Treacy | 260/466 |
| 2,831,882 | 4/1958 | Spaeth | 260/466 |
| 4,229,591 | 10/1980 | Nishimura et al. | 260/466 |

FOREIGN PATENT DOCUMENTS 586022  3/1947  United Kingdom ............... 260/466

*Primary Examiner*—Teddy S. Gron
*Attorney, Agent, or Firm*—Garry L. Wamer

[57] ABSTRACT

A vapor phase process for making methyl or ethyl nitrite from methanol or ethanol, respectively, by reacting a nitrogen oxide composition with methanol or ethanol.

20 Claims, 2 Drawing Figures

PREPARATION OF NITRITE ESTERS

This application is a continuation-in-part of Ser. No. 227,798, filed Jan. 23, 1981, now abandoned, commonly assigned.

FIELD OF THE INVENTION

This invention relates to a novel vapor phase process for the preparation of nitrite esters. More particularly, the present invention relates to the preparation of nitrite esters of methanol or ethanol produced in a vapor phase synthesis from the reaction in critical proportions of methanol or ethanol and a nitrogen oxide composition under relatively mild operating conditions.

BACKGROUND OF THE INVENTION

Nitrite esters, i.e., esters of nitrous acid, are generally colorless liquids which have found use in areas such as additives to motor fuels, stabilizers for vinyl compounds, as spasmolytic agents, as reagents for diazotization and as reagents for chemical synthesis.

The classical method for preparing nitrite esters involves the liquid phase reaction of sodium nitrite and sulfuric acid with a desired alcohol. The reaction is normally carried out at ice temperatures, due to the extremely exothermic nature of the reaction, to form nitrite esters as follows:

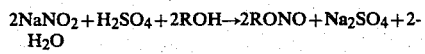

The nitrite ester formed is insoluble in water (less than about 1 percent in water or water in the nitrite ester) so that the nitrite ester is easily separated from the reaction products.

The production of nitrite esters in the liquid phase is disclosed in U.S. Pat. No. 2,166,698 wherein nitrite esters are produced by reacting an appreciably water soluble open-chain saturated aliphatic compound containing a plurality of esterifiable carbinol groups with nitrous acid in an aqueous medium and removing a nitrite ester from the reaction system substantially as soon as it is formed therein. The nitrite esters formed therein react rapidly with alcohol by ester interchange, e.g., ethyl alcohol, to form an alkyl nitrite, e.g., ethyl nitrite.

U.S. Pat. No. 2,739,166 describes producing alkyl nitrites in a liquid phase process by bubbling nitrogen dioxide gas into a cooled liquid monohydric aliphatic alcohol.

In British Patent Specification No. 586,022, a liquid phase process is disclosed for the preparation of nitric acid esters which comprises reacting an alcohol with nitrogen tetroxide in the liquid phase.

German Patentschrift No. 1,156,775 discloses a liquid phase process for preparing esters of nitrous acid by continuously removing the formed ester by employing alcohol in molar excess over dinitrogen trioxide at temperatures below the boiling point of the alcohol and simultaneously distilling off the ester formed. In addition, the reference acknowledges that the vapor phase decomposition of alcohols with nitrogen dioxide-nitrogen monoxide mixtures at temperatures between 100° and 420° is known.

Japanese Application No. 53-8268/78 describes the preparation of nitrite esters by a conventional liquid phase process as part of the continuous production of oxalic acid diester using nitrite ester as a starting material. The nitrous acid ester in the process if formed by employing a common gas-liquid contacting apparatus to react nitrogen oxides with an alcohol at a temperature lower than the boiling point of the alcohol.

The aforementioned processes are to be distinguished from a vapor phase process in that in liquid phase processes the separation of the nitrite ester product is difficult and oxidation of alcohol in the liquid phase during the manufacture or separation can occur to form unwanted by-products. In addition, the separation of the highly flammable and toxic nitrite ester from the liquid phase can prove to be a major safety and health problem.

A vapor phase process is disclosed in U.S. Pat. No. 2,831,822. This patent discloses a process for the preparation of nitrite esters which comprises reacting a vaporized alcohol with from 0.4 to 0.6 mole of nitrogen dioxide and 0.4 to 2.0 moles of nitric oxide per mole of alcohol in the presence of from 2 to 25 moles of diluent which may be water, nitrogen, or carbon dioxide, at a temperature between 100° C. and 420° C. with a contact time of 1-10 seconds.

Table 1 of U.S. Pat. No. 2,831,882 describes 4 examples wherein the molar ratio of NO to $NO_2$ is greater than one but wherein the molar ratio of alcohol to combined NO and $NO_2$ needed to react with all the $N_2O_3$ possible, is less than 1. In each case, in order to achieve a relatively high conversion, above 80%, it was necessary to employ temperatures in excess of about 130° C. In addition to the increased rate of decomposition of nitrite ester (product) at these temperatures, the reference creates additional problems by requiring the employment in each example of a significant amount of water. The use of water in the process results in the formation of nitric acid at least some of which will be present in the ester product.

Table II of U.S. Pat. No. 2,831,882 describes examples which employ various molar ratios of nitric acid, nitrogen dioxide, nitric oxide and nitrogen dioxide or nitric acid to alcohol (n-butanol). In each example the molar ratio of alcohol to total nitrogen oxides is less than one. Further, in each example a temperature in excess of 170° C. was required to provide a conversion to nitrite ester product greater than 70 percent. In addition, the patent, at column 3, lines 55 to 64, states that:

"When nitrogen dioxide is reacted with the alcohol in the presence of water at temperatures below 250° C., equimolar proportions of the nitrite ester and nitric acid are formed. By increasing the temperature of the reaction to 350° C., the formation of nitric acid was almost eliminated, and the conversion to nitrite ester increased. These results are consistent with the previously mentioned mechanism of reaction, since a higher temperature increases the decomposition of both nitric acid and nitrogen dioxide."

Thus, not only does the process require relatively high temperatures but also results in the formation of nitric acid which may be decomposed at higher temperatures.

Examle 1 of U.S. Pat. No. 2,831,882 prepares the nitrite of isopropyl alcohol. This example in U.S. Pat. No. 2,831,882 provides a molar ratio of NO to $NO_2$ of less than one and an isopropanol to a combined NO and $NO_2$ molar ratio of greater than one. The process is operated at a pressure of 90 psi with only a 58 percent conversion to product (the reference reports a yield of 89% based, presumably, on nitrite ester converted from the alcohol consumed which in reality is a conversion of about 39 percent based on the nitric oxide and nitrogen dioxide available). In addition, the process results in the incomplete reaction of the nitrogen dioxide. The unreacted nitrogen dioxide may be quite deleterious to any further process in which the nitrite ester is employed.

U.S. Pat. No. 4,229,591 uses the preparation of nitrite esters as an intermediate step in a process for preparing a diester of oxalic acid. The patent discloses, at Col. 2, lines 21–35, that:

> The nitrogen compound used in the present process need not necessarily be in the form of an ester of nitrous acid, and a compound which forms an ester of nitrous acid in the reaction system may also be used. It may also be advantageous to use an alcohol along with a nitrogen compound selected from the group consisting of nitrogen monoxide, nitrogen dioxide, dinitrogen trioxide and dinitrogen tetroxide, and hydrates of a nitrogen oxide instead of an ester of nitrous acid by introducing a gas containing molecular oxygen into the system in cases where nitrogen monoxide is used. As the hydrates of a nitrogen oxide may effectively be used nitric acid, nitrous acid and the like. An alcohol to be used in such cases is selected from alcohols which constitute esters of nitrous acid as mentioned hereinbelow.

To overcome the problems associated with the known processes for the preparation of nitrite esters a process must be found that may be run in the vapor phase at relatively low temperatures and pressures while minimizing the formation of by-products.

The aforementioned processes fail to appreciate the need to provide a vapor phase process wherein the molar ratio of nitric oxide (NO) to nitrogen dioxide ($NO_2$) and the molar ratio of alcohol to the combined molar quantity of nitric oxide and nitrogen dioxide are each greater than one in order to effect an efficient process, one which can run at relatively low temperatures and pressures while minimizing the formation of by-products.

SUMMARY OF THE INVENTION

This invention relates to a process for making methyl or ethyl nitrite from methanol or ethanol, respectively, which comprises reacting in the vapor state in a reaction zone (i) a molar amount of a nitrogen oxide composition containing a nitric oxide to nitrogen dioxide molar ratio of greater than 1, with (ii) a molar amount of vaporized methanol or ethanol wherein the molar ratio of methanol or ethanol to the molar amount of the nitrogen oxide composition is greater than one. The reaction is carried out in the presence of an inert gaseous diluent for said reaction, and at a temperature of at least about 10° C. to about 300° C., at a pressure, preferably atmospheric or superatmospheric pressure, for a period of time sufficient to form methyl or ethyl nitrite.

DETAILED DESCRIPTION

There is herein described a process for the preparation of nitrite esters, particularly for the manufacture of methyl and/or ethyl nitrite. The process may be understood more fully by reference to the following equations:

$$2NO + O_2 \rightarrow 2NO_2 \quad (1)$$

$$NO_2 + NO \rightleftharpoons N_2O_3 \quad (2)$$

$$2ROH + N_2O_3 \rightarrow 2RONO + H_2O \quad (3)$$

$$ROH + N_2O_3 \rightarrow RONO + HONO \quad (4)$$

$$ROH + HONO \rightarrow RONO + H_2O \quad (5)$$

$$2NO_2 \rightleftharpoons N_2O_4 \quad (6)$$

$$ROH + N_2O_4 \rightarrow RONO + HNO_3 \quad (7)$$

wherein R is methyl or ethyl.

Since the goal of the process is to maximize the production of methyl or ethyl nitrite while minimizing, preferably essentially eliminating, the formation of nitric acid as well as other by-products, the reaction characterized by equations (1), (2), (3) are integrated in reaction (4) which supplies the nitrous acid for reaction (5). That reaction sequence is preferred while the reactions characterized by equations (6) and (7) are to be minimized because of the formation of nitric acid.

It has been found that by providing NO, $NO_2$ and ROH in specific molar ratios that alkyl nitrite may be formed in high yield with minimal formation of nitric acid. To achieve these results the molar ratio of nitric oxide to nitrogen dioxide must be provided such that is is greater than one and the molar ratio of alcohol to the combined molar amount of nitric oxide and nitrogen dioxide is greater than one. The correlation of these two molar ratios provides the process of this invention.

In carrying out the process the source of the reactants is not critical. Nitric oxide may be provided by the decomposition of nitric acid and/or nitrogen dioxide, or may be introduced from a source such as an ammonia oxidation unit. The process will generally be carried out by introducing nitric oxide and oxygen to form the required amounts of nitrogen dioxide (see equation (1)). The molar ratio of nitric oxide to nitrogen dioxide is maintained above one in this case by providing nitric oxide and oxygen at a molar ratio of greater than 4 to 1 such that the molar ratio of nitric oxide to the nitrogen dioxide is greater than 1. A gaseous medium having the desired ratio of nitric oxide to nitrogen dioxide may be obtained by use of higher oxides of nitrogen ($N_2O_3$, $N_2O_4$, $N_2O_5$, etc.) and to the extent that such higher oxides may be employed to provide a gaseous medium, with or without the addition of molecular oxygen, having a molar ratio of NO to $NO_2$ greater than 1, said higher oxides may be employed herein. In addition, compounds such as nitrous acid, which can decompose and react to provide a gaseous medium having a molar ratio of NO to $NO_2$ greater than one may be employed.

As noted above, the process is preferably carried out by forming the desired molar ratio of NO to $NO_2$ by reacting molecular oxygen and NO at a molar ratio of 4 to 1 or greater. Though the process may be carried out by mixing nitric oxide, oxygen, and alcohol (methanol or ethanol) together at the desired molar ratios, such mixing may be undesirable because oxygen will oxidize the alcohol (methanol or ethanol) to a variety of undesirable reaction products with the consequential loss of valuable starting material and result in the possible formation of flammable compositions which may present a safety hazard. Such undesirable reaction products, as contaminants of the nitrite, can prove deleterious to the use of the alkyl nitrite in subsequent reactions such as the formation of alkyl oxalates by the process of U.S. Pat. No. 4,229,591. Therefore, the process is preferably carried out such that nitric oxide and molecular oxygen are mixed for a sufficient time for the reaction (see equation (1) above) to consume the oxygen prior to mixing the resulting nitrogen oxide mixture (a mixture having a molar ratio of NO to $NO_2$ greater than 1) with the alcohol.

The process is carried out in the presence of an inert gaseous diluent to moderate the reaction to preclude the formation of explosive mixtures and prevent the formation of excessive amounts of undesirable by-products. When carrying out the process the inert gaseous diluent is added either concurrently with the nitric oxide or with the molecular oxygen, or with both. Further, inert gaseous diluent may be added to carry and vaporize the alcohol. As the inert gaseous diluent, it is preferred to employ nitrogen, carbon dioxide or other inert gaseous compounds. The use of carbon dioxide provides higher heat capacity relative to nitrogen. Carbon monoxide may be present and used as a diluent although its concentration in the reaction system must be carefully controlled to prevent the formation of flammable mixtures. The inert gaseous diluent is employed in a sufficient amount to provide the aforementioned objectives. The inert diluent is generally employed in the process such that between about 1 and about 99 mole percent, preferably between about 30 and about 90 mole percent, and most preferably between about 30 and about 70 mole percent, is inert gaseous diluent. The exact amount of inert gaseous diluent will, in part, be determined by the selected ester of nitrous acid and the selected process parameters, e.g., temperature and pressure.

According to the invention, the process is carried out at a temperature between about 10° C. and about 300° C., preferably between about 20° C. and about 130° C. and most preferably between about 50° C. and less than about 110° C. The lowest temperature at which the process is conducted is generally determined by the dew point of the alcohol employed and the concentration of reactants.

The pressure at which the process is carried out is not narrowly critical. Preferably, atmospheric or superatmospheric pressure is employed, more preferably between about atmospheric (14.7 psia) and about 100 psia and most preferably at between about 20 psia and about 60 psia. Pressures less than 14.7 psia may be employed, if desired.

The process is preferably carried out with reactants which are essentially anhydrous since the presence of water in the reactants fosters the formation of undesirable by-products which must be separated ultimately if the ester of nitrous acid is to be subsequently employed in further processes. It is preferred to carry out the process such that the amount of water provided by the reactants is minimized. It should be remembered that the reaction forms water and such formed water must be tolerated.

As stated, the molar ratio of nitric oxide to nitrogen dioxide is greater than 1. Typically the molar ratio (NO to $NO_2$) will be from greater than 1 to about 10, preferably from greater than 1 to about 2 and most preferably from greater than 1 to about 1.5. The molar ratio of alcohol (methanol or ethanol) to the combined molar amount of nitric oxide and nitrogen dioxide is greater than one. The term "combined molar amount" means the numerical sum of the molar amount of NO and $NO_2$ that react according to reaction (2), above. Typically the molar ratio of ROH to (NO+$NO_2$) will be from greater than 1 to about 10, preferably from greater than 1 to about 2 and most preferably from greater than 1 to about 1.5.

The process of this invention may be practiced in almost any commercial reactor and is generally carried out on a continuous basis by employment of a tubular reactor. The contact time (or residence time in the reactor) during which the gaseous materials react to form methyl or ethyl nitrite is generally from about 0.1 to about 30 seconds, preferably 0.1 to about 2 seconds. Shorter or longer times may be employed depending on the temperature, pressure, molar ratios, diluent and feed rate employed so long as sufficient time for reaction is provided. In addition, the selection of the reactor geometry of the nitrite forming reaction zone will affect the actual residence time employed.

When the process is carried out in a continuous manner the feed rate is not narrowly critical, and is selected to satisfy the particular design of the continuous system.

The following description of the Figures and the Examples are provided to illustrate this invention and are not intended to limit, in any way, the scope of this invention.

DESCRIPTION OF FIGURES

Referring to FIG. 1, methanol or ethanol (labeled alcohol) is introduced as a liquid or vapor into line 10 and mixed with inert diluent, designated here as nitrogen, at point 12. The stream in line 10 passes to preheater 14 and exits preheater 14 via line 16 in the vapor state.

Figure 1:
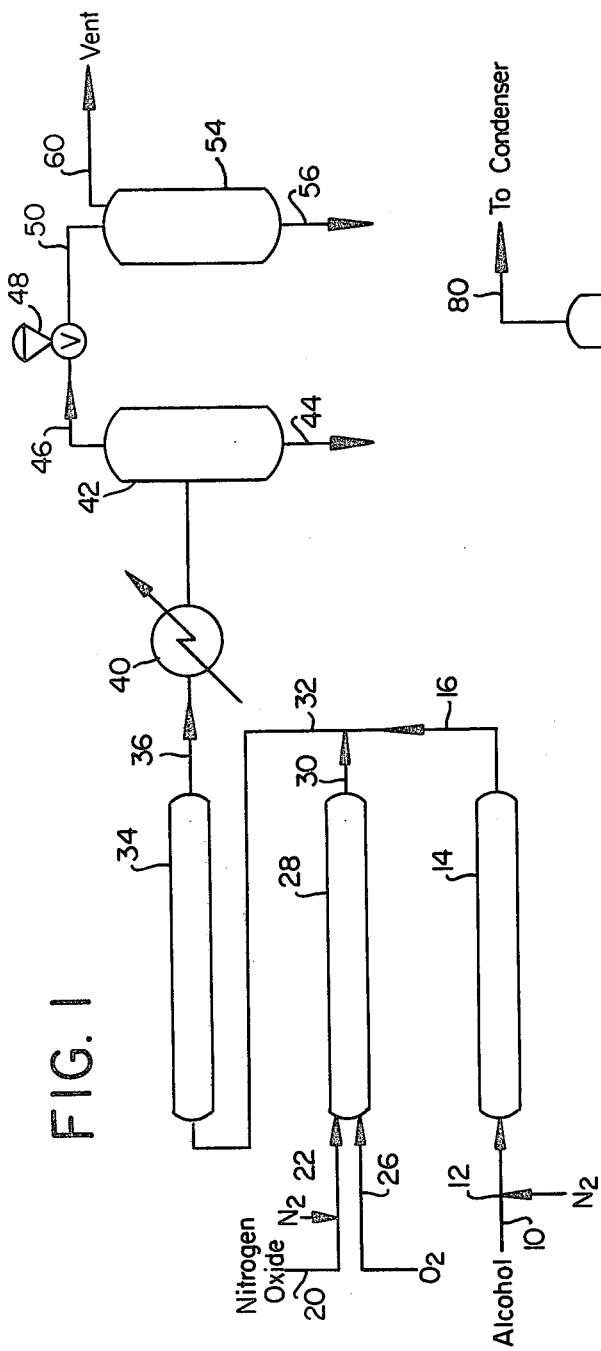
FIG. 1 schematically depicts the design and operation of an apparatus employing a tubular reactor for carrying out the process of the invention.

A nitrogen oxide (preferably NO) is introduced in line 20 and inert diluent, designated here as nitrogen, is added at point 22 of line 20. The order of addition is not critical. Line 26 for adding molecular oxygen is provided for use when nitric oxide is employed as the nitrogen oxide. When nitric oxide is the selected nitrogen oxide, the gaseous streams in lines 20 and 26 are fed to oxidizer 28 for formation of higher oxides of nitrogen. The gaseous stream exiting oxidizer 28 via line 30 is admixed with the contents of gaseous stream 16 and the combined stream is fed through line 32 to nitrite reactor 34 wherein the reaction products methyl nitrite or ethyl nitrite are formed. The reaction products as well as any other stream constituents (such as nitrogen oxides, alcohol, and formed water) exit nitrite reactor 34 via line 36 to heat exchanger (condenser) 40 maintained at a temperature to condense a substantial or desired amount of unreacted alcohol and formed water. The condensed gaseous alkyl nitrite containing mixture is then fed to a vapor-liquid separator 42 wherein water, excess alcohol and the like are separator and collected via line 44. The vaporous alkyl nitrite stream exits vapor-liquid separator 42 via line 46 and passes through a pressure regulator 48 (which controls the process pressure) and is introduced via line 50 to product condenser 54 (optional) if condensed alkyl nitrite is to be obtained. Condensed alkyl nitrite product is collected via line 56. Uncondensed gaseous products exit product condenser 54 via line 60 (vent) and are treated to remove harmful components contained therein or are recycled to line 20.

Figure 2:
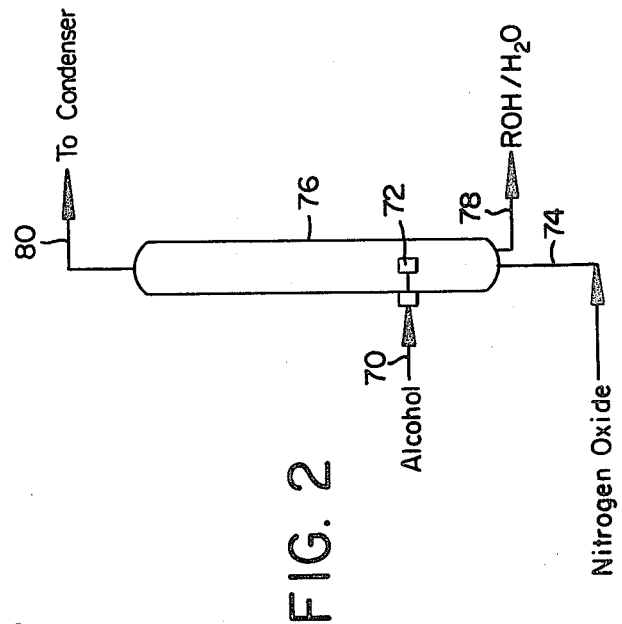
FIG. 2 schematically depicts a particular reactor design for preparing alkyl nitrites.

FIG. 2 schematically depicts a nitrite reactor wherein a nitrogen oxide is introduced to nitrite reactor 76 through line 74. If the nitrogen oxide is nitric oxide a feed line is provided for introducing molecular oxygen (not shown) to line 74 prior to reactor 76. Alcohol mixed with nitrogen is introduced through line 70 and vaporized (fine aerosol dispersion) through vaporizer 72. Methyl nitrite or ethyl nitrite formed in nitrite reactor 76 exits through line 80, as well as other gaseous constituents, to a condenser (such as heat exchanger 40 of FIG. 1). Some alcohol and water may condense in reactor 76 and exits through line 78. Nitrite reactor 76 may be packed or unpacked, as desired, but is preferably packed with inert material especially in the space above vaporizer 72. The condensed product is then treated similarly as was the condensed product of FIG. 1.

In addition, it has been observed that it may be preferred to carry out the process in such a manner that the reactions characterized by equations (4) and (5), as previously discussed, are considered in carrying out the process. In such a case the process is carried out in two reaction zones. The first reaction zone is generally a tubular reaction zone such as that depicted for nitrite reactor 34 of FIG. 1 and is designed to minimize the back-mixing in the first reaction zone as the reaction characterized by equation (4) proceeds. Such tubular reactor or other similar reactor may be packed or unpacked, as desired. The second reaction zone is designed to take into account the ionic nature of the reaction characterized by equation (5). The nitrige reactor shown in FIG. 2 is suitable for such second reaction zone and is preferably packed with an inert material, e.g., glass beads and the like, located such that a wet surface is provided by maintaining the temperature and pressure in the second reaction zone at just above the dew point of the alcohol (methanol or ethanol) being employed. It has been observed that by employing two such reaction zones that the formation of by-products can be greatly minimized. Such minimized formation of by-products is of great importance when subsequent use of the alkyl nitrite is desired and reduces the extent of purification, if any, of the alkyl nitrite required.

EXPERIMENTAL PROCEDURE

The examples were carried out employing the apparatus as depicted in FIG. 1 and where indicated, using the reactor of FIG. 2 for the simple tube reactor shown in FIG. 1. When the apparatus as depicted in FIG. 1 was employed the oxidizer (NO oxidizer) was a 6 feet No. 304 stainless steel tube having a ⅜ inch, outside diameter (0.31 inch inside diamater). The alcohol preheater was a 6 feet No. 304 stainless tube having a ½ inch outside diameter (0.435 inch inside diameter) packed with a stainless steel sponge throughout. The nitrite reactor was a tube reactor 17 feet in length of No. 304 stainless steel tube with a ⅜ inch outside diameter (0.31 inch inside diameter). The three aforementioned stainless steel tubes were heated in a common heating bath of ethylene glycol.

The reactor of FIG. 2 was made from a Hoke [304 stainless steel, 400 psig 4LS500] cylinder having an internal volume of about 530 cubic centimeters. The reactor was fitted with a side arm 3¼-in from the bottom. An ALL TECH (TM) Low Pressure Solvent Filter (ALL TECH Associates) with ⅛-in outside diameter tubing (Cat. No. 9402 Hasteloy (TM) stainless steel) was fitted through the side arm and was fitted with a fritted opening at its terminus. The bottom of the reactor was fitted with a gas inlet tube which was positioned just below the vaporizer and a take-off valve to drain any reactor liquid. The reactor was heated electrically through electrical wrapping about the reactor cylinder. The alcohol feed, with or without nitrogen as the gaseous diluent, was fed through the side arm and forced through the frit to form a fine aerosol dispersion of alcohol, while the nitrogen oxide/nitrogen mixture was fed through the gas inlet.

The vaporous stream from the nitrite reactor (one of the above-described) was fed to a condenser formed from a 21' by ⅜" outside diameter (0.31 inch inside diameter) No. 304 stainless steel tube cooled in an ice-water bath. The partially condensed stream was then fed to a vapor-liquid separator (at ice water temperature) and subsequently to a product condenser (at ice water temperature) made from 5 inch Schedule 10S No. 304 stainless steel piping (11 inches in length). The various lines of the apparatus are formed of ¼" outside diameter (0.185 inch inside diameter) stainless steel tubing. Nitrogen oxide, oxygen and carbon monoxide were introduced by use of pressure differential control with stainless steel capillary-type orifice nipples. The pressure was controlled with a Grove Pressure regulator (Model No. SD 91 LW (35254-315)) with Teflon seals. The pressure on the Grove regulator was controlled with a Moore 4300-35353-299 bleed-type regulator. The alcohol was metered into the process using a metering pump from Fluid Metering Inc. (Model RP-650-OSSY).

The condensed material from the vapor-liquid condenser and the product condenser were analyzed by vapor phase chromatography.

EXAMPLES 1 and 2

The process according to this invention was carried out employing the scheme depicted in FIG. 1 except that the reactor of FIG. 2 was employed in Example 1 instead of the tube reactor 34 of FIG. 1. The results of the Examples are set forth in Table I. The molar ratio of nitric oxide to nitrogen dioxide (formed from a mixture of nitric oxide and molecular oxygen) was greater than one and the molar ratio of alcohol to combined molar amount of nitric oxide and nitrogen dioxide was greater than one.

COMPARATIVE EXAMPLE 3

Comparative example 3 was carried out as set forth in Example 3 of Table I.

TABLE 1

| Example No. | Flows, SCFH[2] | | | NO/NO₂[3] | EtOH[4] ml/hr | $\frac{\text{EtOH}[4]}{(\text{NO} + \text{NO}_2)}$ | Nitrite Reactor | | | Condenser[5] | | V.L.[6] | |
|---|---|---|---|---|---|---|---|---|---|---|---|---|---|
| | | | | | | | Temp., °C. | | Pres. | Temp., °C. | | Sep. | Time |
| | N₂ | NO | O₂ | | | | Inlet | Outlet | psig | Inlet | Outlet | Press | Hrs. |
| 1 | 1.45 | 0.9 | 0.174 | 1.62 | 65 | 1.26 | 94 | 78 | 15 | 63 | 8 | 29.7 | 6.08 |
| 2 | 6.00 | 0.9 | 0.174 | 1.62 | 60 | 1.17 | 97 | 82 | 15 | 82 | 11 | 29.7 | 8.15 |
| 3 | 1.45 | 0.9 | 0.26 | 0.73 | 60 | 1.07 | 115 | 95 | 15 | 84 | 10 | 29.7 | 5.0 |

| Example No. | Product, grams | | | | | | |
|---|---|---|---|---|---|---|---|
| | Total | ETONO[7] | ETOH[8] | H₂O | Acetald.[9] | Ethyl Formate | Acidity as HNO₃[10] |

TABLE 1-continued

| | | | | | | | |
|---|---|---|---|---|---|---|---|
| 1 | 551.5 | 356.1 | 151.8 | 41.9 | 0.12 | 0.25 | 1.44 |
| 2 | 632.5 | 376.2 | 194.7 | 60.8 | 0.18 | nd[1] | 14.5 |
| 3 | 492.4[11] | 274.4 | 154.1 | 52.6 | 6.0 | 3.2 | 14.5 |

[1]None detected
[2]Flow in standard cubic feet per hour
[3]Molar ratio of nitric oxide to nitrogen dioxide
[4]Ratio of ethanol to combined molar ratio of (NO + NO$_2$)
[5]Inlet and outlet temperatures of condenser 40 of FIG. 1Pressure in Vapor-liquid (V.L.) separator, psia
[7]Ethyl nitrite
[8]Ethanol
[9]Acetaldehyde
[10]Acid present calculated as nitric acid
[11]Ethyl acetal also present (0.4 grams)

We claim:

1. The process for making methyl or ethyl nitrite from methanol or ethanol, respectively, which comprises reacting in a reaction zone a molar amount of nitrogen oxide composition containing a nitric oxide to nitrogen dioxide molar ratio of greater than 1, in the vapor state, with a molar amount of vaporized methanol or ethanol wherein the molar ratio of methanol or ethanol to the combined molar amount of nitric oxide and nitrogen dioxide is greater than one, in the presence of an inert gaseous diluent for said reaction, at a temperature of between about 10° C. to about 300° C. for a period of time sufficient to form methyl or ethyl nitrite.

2. The process of claim 1 wherein the inert gaseous diluent is nitrogen.

3. The process of claim 1 wherein the inert gaseous diluent is carbon dioxide.

4. The process of claim 2 or 3 wherein the inert gaseous diluent is present in an amount between about 1 percent and about 99 percent by volume.

5. The process of claim 4 wherein the inert gaseous diluent is present in an amount between about 30 percent and about 90 percent by volume.

6. The process of claim 1 wherein the nitrogen oxide comprises nitric oxide and molecular oxygen in a molar ratio of nitric oxide to molecular oxygen of greater than 4 to 1.

7. The process of claim 1 wherein said process is carried out under essentially anhydrous conditions.

8. The process of claim 1 wherein the process makes methyl nitrite from methanol.

9. The process of claim 1 wherein the process makes ethyl nitrite from ethanol.

10. The process of claim 1 wherein the temperature is between about 20° C. and about 130° C.

11. The process of claim 10 wherein the temperature is between about 70° C. and less than 110° C.

12. The process of claim 1 wherein the process is carried out at atmospheric (14.7 psia) or superatmospheric pressure.

13. The process of claim 12 wherein the pressure is between about atmospheric (14.7 psia) and about 100 psia.

14. The process of claim 13 wherein the pressure is between about 20 psia and about 60 psia.

15. The process of claim 1 wherein the molar ratio of nitric oxide to nitrogen dioxide and the molar ratio of methanol to ethanol to combined molar amount of nitric oxide and nitrogen are each, respectively, between greater than 1 to about 10.

16. The process of claim 15 wherein the molar ratios are each, respectively, between greater than 1 to about 2.

17. The process of claim 16 wherein the molar ratios are each, respectively, between greater than 1 to about 1.5.

18. The process of claim 1 wherein at least a portion of the inert gaseous diluent is carbon monoxide.

19. The process for making methyl or ethyl nitrite in the vapor state wherein:
   (a) methanol or ethanol is introduced under pressure into a body having an internal volume;
   (b) said alcohol is vaporized;
   (c) a nitrogen oxide having a nitric oxide to nitrogen dioxide ratio greater than 1 is introduced under pressure into said body;
   (d) the resulting mixture of steps (a), (b) and (c) is characterized as having a molar ratio of methanol or ethanol to nitrogen oxides of greater than 1; and
   (e) removing said methyl or ethyl nitrite from said body.

20. The process of claim 19 wherein the unreacted alcohol and water are removed in a step (f).

* * * * *